US010245414B2

(12) United States Patent
Melsheimer et al.

(10) Patent No.: US 10,245,414 B2
(45) Date of Patent: Apr. 2, 2019

(54) MEDICAL DEVICE WITH SELECTIVE RIGIDITY

(71) Applicant: Cook Medical Technologies LLC, Bloomington, IN (US)

(72) Inventors: Jeffry S. Melsheimer, Springville, IN (US); Robert M. Eells, Bloomington, IN (US); Kristen Van Wyk, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 121 days.

(21) Appl. No.: 14/851,802

(22) Filed: Sep. 11, 2015

(65) Prior Publication Data

US 2017/0035988 A1    Feb. 9, 2017

Related U.S. Application Data

(63) Continuation of application No. PCT/US2014/023159, filed on Mar. 11, 2014.

(60) Provisional application No. 61/791,561, filed on Mar. 15, 2013.

(51) Int. Cl.
*A61M 25/00* (2006.01)
*A61B 17/02* (2006.01)
(Continued)

(52) U.S. Cl.
CPC ..... *A61M 25/0054* (2013.01); *A61B 17/0218* (2013.01); *A61F 2/82* (2013.01);
(Continued)

(58) Field of Classification Search
CPC .......... A61M 25/1011; A61M 25/0054; A61M 25/0053; A61M 25/0052; A61M 25/005;
(Continued)

(56) References Cited

U.S. PATENT DOCUMENTS 4,815,450 A * 3/1989 Patel .................. A61B 1/00078
600/115
5,275,610 A    1/1994 Eberbach
(Continued)

FOREIGN PATENT DOCUMENTS

WO    WO 2012/071105 A1    5/2012

OTHER PUBLICATIONS

U.S. Office Action dated Aug. 21, 2015, for U.S. Appl. No. 14/203,007, 13 pp.
(Continued)

*Primary Examiner* — Kami A Bosworth
*Assistant Examiner* — Alexandra Lalonde
(74) *Attorney, Agent, or Firm* — Brinks Gilson & Lione

(57) ABSTRACT

A device for obtaining selective rigidity with respect to a patient is provided. The device includes a scaffold that is arranged to be flexible when in a first relaxed configuration, wherein the scaffold is configured to become substantially more rigid when a suction force is applied thereto. The scaffold comprises first and second opposing outer flexible layers that are sealed together to form a plurality of elongate pockets therein, and an expanded structure disposed within the plurality of elongate pockets and in communication with a vacuum port that receives the suction force.

18 Claims, 15 Drawing Sheets

(51) Int. Cl.
 *A61F 2/82* (2013.01)
 *A61M 25/10* (2013.01)
 *A61F 2/90* (2013.01)
(52) U.S. Cl.
 CPC . *A61M 25/1025* (2013.01); *A61B 2017/0225* (2013.01); *A61F 2/90* (2013.01); *A61F 2250/0003* (2013.01); *A61F 2250/0018* (2013.01)
(58) Field of Classification Search
 CPC .............. A61M 25/04; A61M 25/1025; A61M 25/0074; A61M 25/008; A61M 2025/1013; A61M 2025/0039; A61M 2025/004; A61M 25/0043; A61M 2025/0063; A61B 17/320725; A61B 1/00078
 See application file for complete search history.

(56) References Cited

U.S. PATENT DOCUMENTS

| | | | |
|---|---|---|---|
| 5,312,432 A | 5/1994 | Pingleton et al. | |
| 5,582,577 A | 12/1996 | Lund et al. | |
| 5,590,778 A * | 1/1997 | Dutchik | B65D 77/04 206/439 |
| 6,293,968 B1 | 9/2001 | Taheri | |
| 8,425,412 B2 | 4/2013 | Rucker | |
| 8,968,188 B2 | 3/2015 | Rockrohr | |
| 2002/0156496 A1* | 10/2002 | Chermoni | A61F 2/958 606/194 |
| 2006/0069346 A1* | 3/2006 | Smith | A61M 25/005 604/95.05 |
| 2007/0065418 A1* | 3/2007 | Vallana | A61K 35/12 424/93.7 |
| 2009/0149710 A1 | 6/2009 | Stefanchik | |
| 2009/0292172 A1* | 11/2009 | Roskopf | A61B 1/00135 600/115 |
| 2013/0066346 A1* | 3/2013 | Pigott | A61B 17/3209 606/159 |

OTHER PUBLICATIONS

International Search Report for PCT/US2014/023159, dated Mar. 9, 2014, 3 pp.
Brown, Eric et al., Universal robotic gripper based on the jamming of granular material, PNAS, Nov. 2, 2010, vol. 107, No. 44, pp. 18809-18814.

\* cited by examiner

MEDICAL DEVICE WITH SELECTIVE RIGIDITY

CROSS-REFERENCE TO RELATED APPLICATIONS

This application is a continuation of International Application Number PCT/US2014/023159, with an international filing date of Mar. 11, 2014, which claimed priority from U.S. provisional application Ser. No. 61/791,561, filed on Mar. 15, 2013, the entirety of which are each hereby fully incorporated by reference herein.

TECHNICAL FIELD

This disclosure relates to expandable and compressible structures for clinical use with respect to a patient.

BRIEF SUMMARY

A first representative embodiment of the disclosure is provided. The embodiment includes a device for obtaining selective rigidity with respect to a patient is provided. The device includes a scaffold that is arranged to be flexible when in a first relaxed configuration, wherein the scaffold is configured to become substantially more rigid when a suction force is applied thereto. The scaffold comprises first and second opposing outer flexible layers that are sealed together to form a plurality of elongate pockets therein, and an expanded structure disposed within the plurality of elongate pockets and in communication with a vacuum port that receives the suction force.

Another representative embodiment of the disclosure is provided. The embodiment includes a medical device. The medical device includes an elongate flexible catheter that extends between a distal end portion and a proximal end portion with a first lumen disposed therethrough, and a second lumen that extends through a wall of the catheter into the distal end portion. The catheter wall comprises a first layer that defines an inner surface of the first lumen and a second layer disposed radially outside of the first layer, and wherein the first and second layers are sealed proximate to a distal tip of the catheter, and the first and second layers establish an interface therebetween that is located within an expandable portion of the catheter wall. The catheter wall further comprises a retention member disposed within the interface between the first and second layers within the distal end portion, and wherein the second lumen establishes fluid communication with the interface. The retention member is urged into a dense configuration under the influence of a vacuum force applied thereto through the second lumen, wherein the retention member is biased to expand to a less dense configuration when the interface is at atmospheric pressure.

Yet another representative embodiment of the disclosure is provided, which includes the medical device described directly above, wherein the retention member is a plurality of particles that are collectively disposed within the interface, the plurality of particles pack tightly with one another and collectively resist deformation when the interface is under the influence of the vacuum force, the plurality of particles are readily movable with respect to each other within the interface when at atmospheric or positive pressure.

Yet another representative embodiment of the disclosure is provided, which includes the medical device described above. The retention member is a compressible foam disposed within the interface between the first and second layers within the distal end portion, wherein the size of the compressible foam decreases and the rigidity increases under the influence of the vacuum force applied to the interface from the second lumen, and the compressible foam is biased to expand and decrease rigidity when at or above atmospheric pressure.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Turning now to FIGS. 1-7, a device 1 for obtaining selective rigidity with respect to a patient is provided. The device 1 may be used to assist with a medical procedure within an internal cavity of a patient (either a human, a mammal or other type of animal). Alternatively, the device 1 may be configured to be used to externally and in some embodiments temporarily with respect to a portion of a patient's anatomy.

Figure 1:
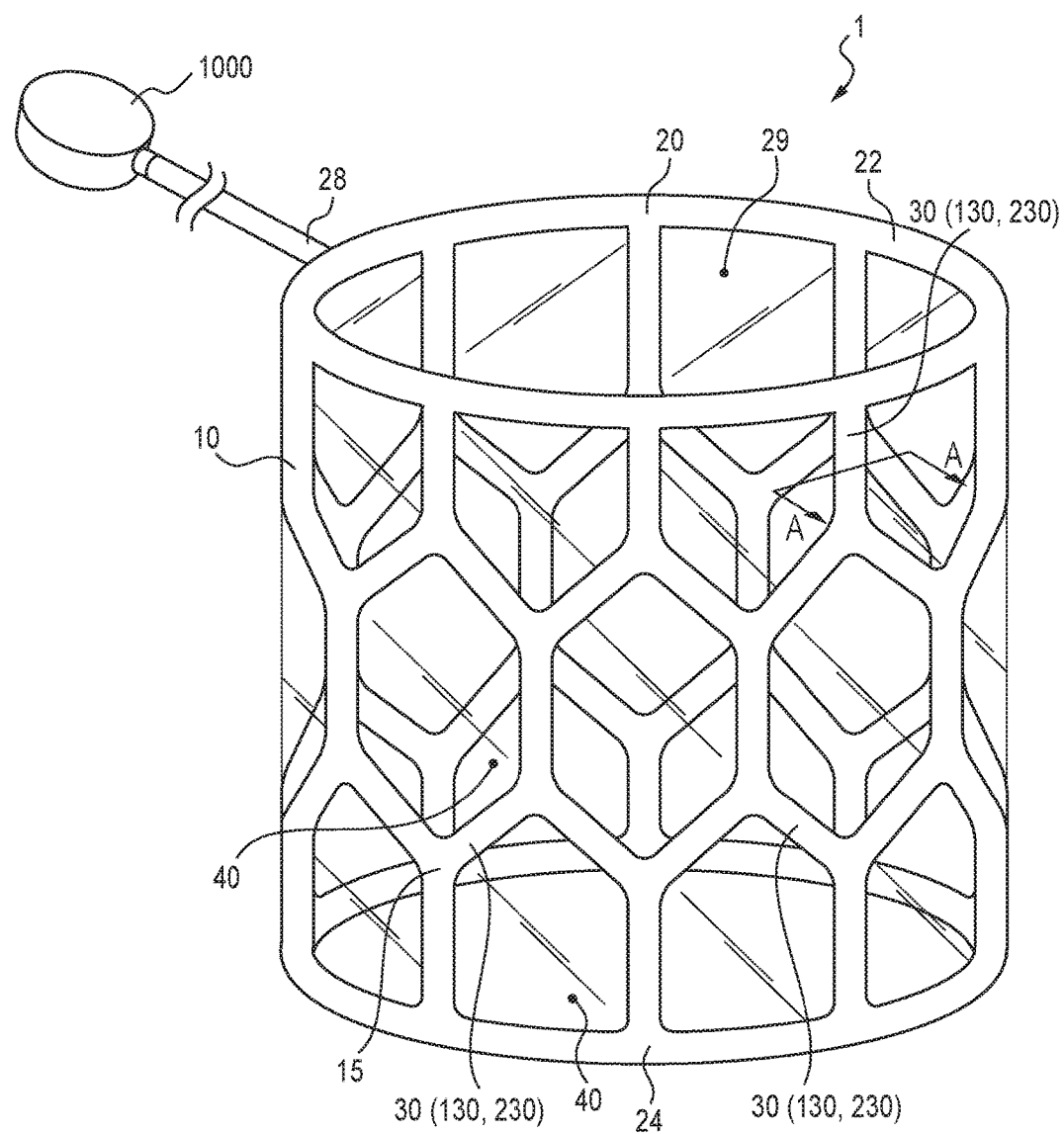
FIG. 1 is a perspective view of a device for selective rigidity formed as a cylinder.

In some embodiments, the device 1 may be formed into a tube or cylinder 10, as shown in FIG. 1. The cylinder 10 will be appreciated to be useful for various open surgical procedures, or various laparoscopic procedures. In some embodiments, the cylinder 10 may include opposed ends 22, 24, while in other embodiments, an extended end 24 (normally that extends further distally into the patient) may be closed, either with a window 40 (discussed below), or with a mesh or other suitable structure, while the opposite end 22 (e.g. an end closer to the vacuum line 28) is open. In other embodiments, both ends 22, 24 of the cylinder may be closed, such as in embodiments where the cylinder 10 is used to position tissue into a certain orientation or position, but where access within the cylinder 10 is not necessary.

By way of general example, in some clinical embodiments, the cylinder 10 may be configured to be used as an internal surgical retractor, or a flexible barrier that may be deployed within a surgical zone to isolate the surgical zone and neighboring tissue or viscera outside of the surgical zone. In other embodiments, the cylinder 10 may be configured to provide temporary or long term mechanical or radial support upon a structure or lumen, and act as a stent. In still other embodiments, the cylinder 10 may be configured to provide external mechanical support to a structure, or temporarily immobilize a structure, such as a cast or a splint.

Figure 2:
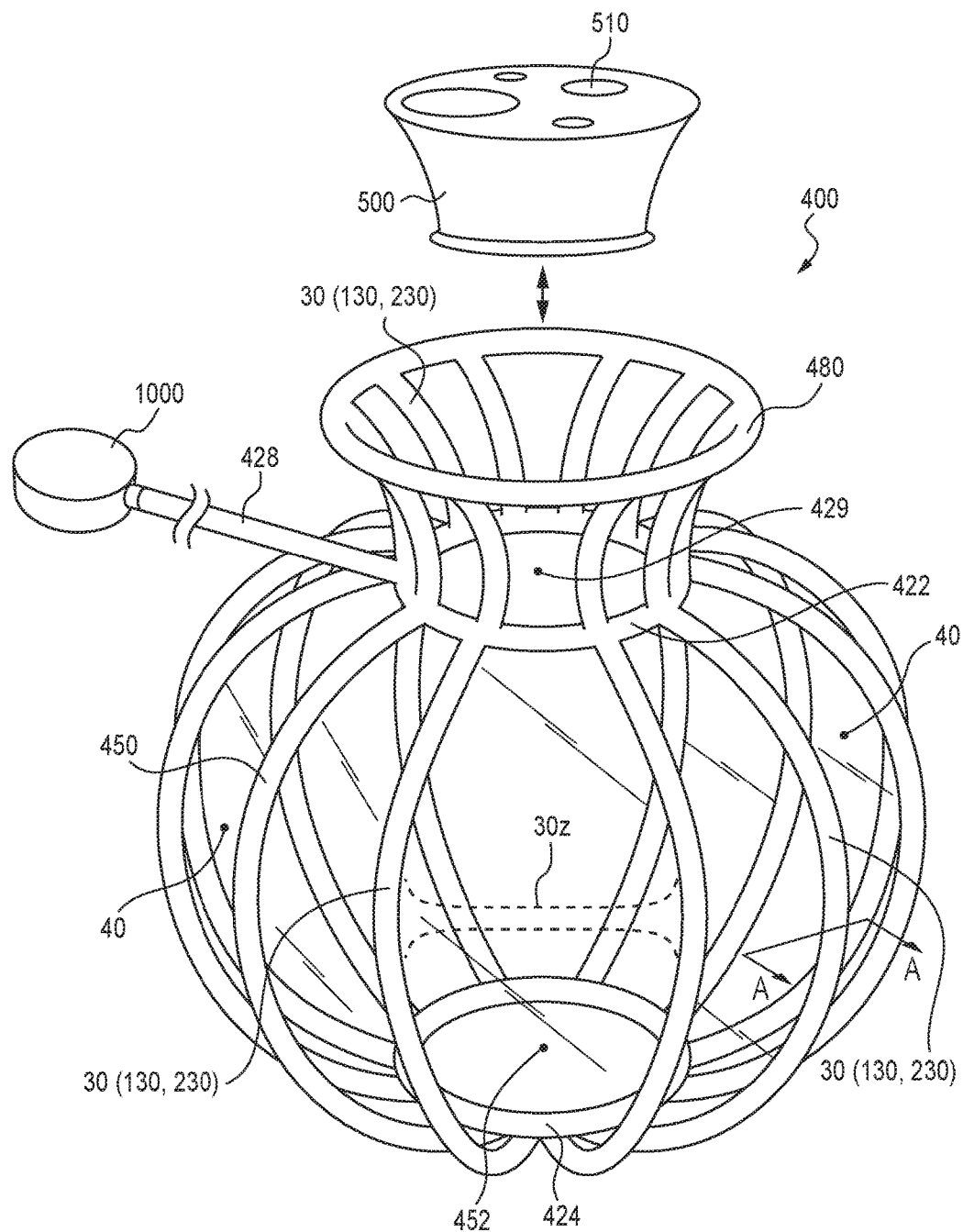
FIG. 2 is a perspective view of a device for selective rigidity formed as a sphere.

In other embodiments as shown in FIG. 2, the device 1 may be formed into a sphere 400 or a similar construction. Embodiments where the device is shaped as a sphere 400 will be appreciated to be applicable or useful for the same or related clinical uses as listed above with respect to the cylinder 10, or other clinical uses where a cylinder is not clinically indicated. By way of clinical example, the sphere 400 may be used as a retractor used during laparoscopic or open surgery. Alternatively, by way of example, the device may be formed as a semi-circle (i.e. half of a hollow sphere) where the device forms a somewhat rigid support structure, such as a bicycle helmet.

Figure 6:
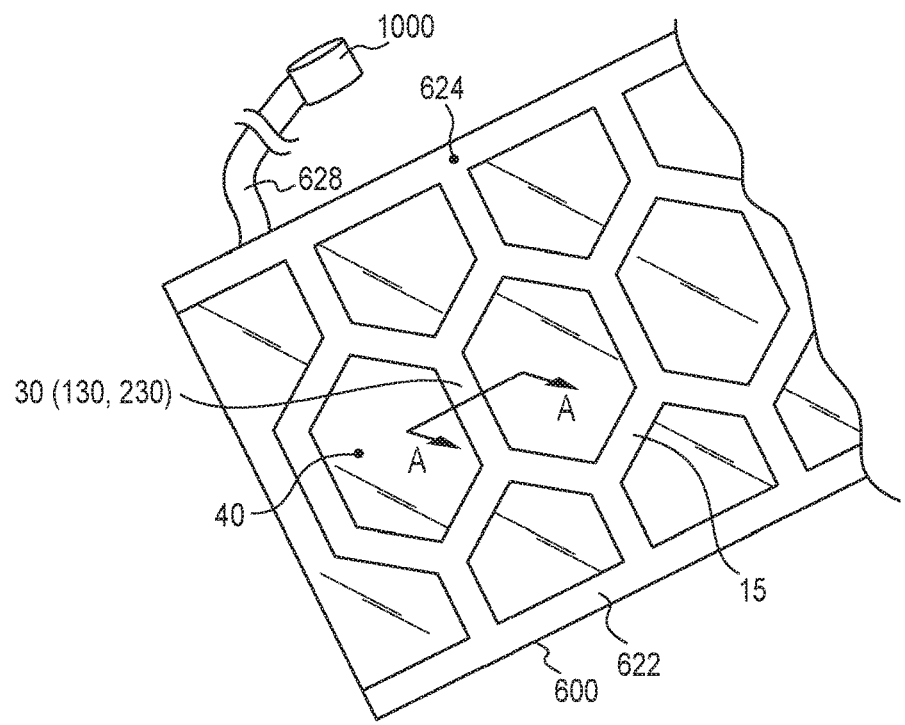
FIG. 6 is a perspective view of a device for selective rigidity formed as a flat sheet.
Figure 6A:
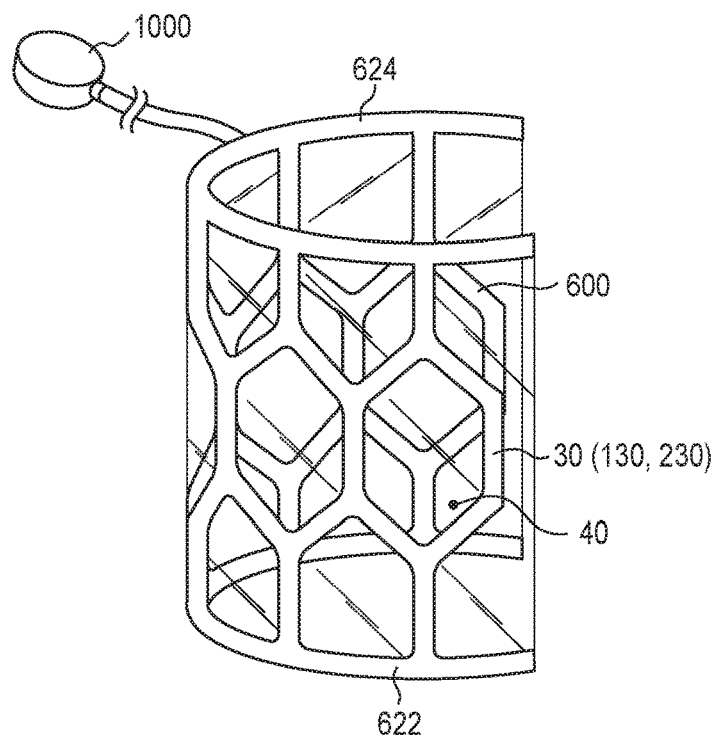
FIG. 6a is the device of FIG. 6 formed into a c-shape.

In still other embodiments shown in FIGS. 6a and 6b, the device 1 may be formed into a sheet 600, which can clinically implemented as a sheet, or can be clinically implemented with the sheet configured into a three-dimensional shape, such as a C-shape depicted on FIG. 6b.

The device 1 is configured to be maintained in a flexible orientation when a plurality of elongate pockets 30 (130, 230) that define a scaffold 15 of the device 1 are in the normal expanded configuration, but the device is configured to become substantially more rigid, and configured to significantly maintain a set geometry when the elongate pockets 30 (130, 230) are placed in communication with a source of suction, which withdraws a significant portion of the air (or other gasses) present within the internal volume 50 of the elongate pockets 30 (130, 230). The device 1 is configured to retain its normal flexibility when the suction is released from the elongate pockets 30 (130, 230), which allows the evacuated air to return to within the internal volume of the elongate pockets 30.

In embodiments where the device is used as a retractor during laparoscopic surgery, the device 1 should be sufficiently compressible into a small cylindrical cross-section to fit through a typical laparoscopic port. This compressibility of the device 1 is based upon the overall compressibility of the foam (or another compressible material) used within the pockets 30 (130, 230), discussed below, and the device 1 can expand on its own when within the patient. In some embodiments, the device 1 may be made to be expandable (particularly after being compressed to extend through a port) by "inflating" the plurality of pockets 30 (discussed below) using the vacuum port 28. In embodiments where the device 1 used in laparoscopic surgery or even in open surgery the vacuum port 28 is configured to communicate outside of the patient to connect to a convenient source of suction 1000 (or positive pressure as discussed above).

Each of the cylinder 10, the sphere 400, or the sheet 600 may be made from the same or a related scaffold 15 design to form the same or similar elongate pockets 30 (130, 230), which are depicted upon the respective cylinder 10, sphere 400, or sheet 600 through section A-A (FIGS. 1, 2, and 6a, respectively). In some embodiments, the scaffold 15 may be formed like a honeycomb, with a plurality of elongate pockets 30 connected together that form structural walls and the spacing between neighboring elongate pockets 30 define a plurality of windows 40. As shown in FIG. 1, the scaffold 15 may be formed with multiple windows 40 arranged across the height of the scaffold 15, between a first end 22 and a second end 24, with the windows 40 staggered, or offset, between the upper and lower ends 22, 24 of the scaffold 15. As discussed herein, in some embodiments, each of the plurality of pockets 30 are fluidly connected together along the scaffold 15, while in other embodiments the pockets 30 are fluidly connected in a groupwise manner.

In other embodiments, the windows 40 may be configured to be aligned along the height and circumference of the scaffold 15, such as a scaffold 15 that defines a plurality of windows 40 that are shaped as stacked squares or rectangles. As will be understood by those skilled in the art with a thorough review of this application, scaffold 15 designs with staggered windows 40 (i.e. like a honeycomb) might be stronger in certain directions (or potentially in all directions) in parallel to the sheets 42, 44 forming the scaffold 15, and potentially in the directions radially into and/or out of the cylinder 10 and therefore better suited for some applications/shapes of the device 1, while designs with stacked windows 40 may be of different/less strength than the staggered design and therefore better suited for use with other applications/shapes of the device 1.

In other embodiments, for example, in some embodiments where the scaffold 15 forms a sphere (e.g. FIG. 2) the scaffold 15 may be formed from a plurality of elongate pockets 30 (130, 230) that form ribs that linearly extend from top 422 to the base 424 of the sphere (to define the curved surface of the sphere), which may form windows 40 that also extend from the top 422 to the base 424 of the sphere. In other embodiments, the scaffold 15 may further include a plurality of horizontal ribs (30*z*, one potential horizontal rib shown in broken lines on FIG. 2) to provide additional structural support to the scaffold 15 and to decrease the size of the windows 40.

In some embodiments, the device 1, such as the cylinder 10 or the sphere 400, as shown in FIG. 2, may receive a cap 500 that removably closes a portion or all of the open top 422 of the device 1. By way of example, the cap 500 may be used in situations where the device 1 is used as a retractor for open surgery, but it is desired to insufflate the abdomen during open surgery or to limit the overall exposure of the surgical field to the atmosphere. In this instance, the cap 500 may include one or more ports 510 that act as laparoscopic ports. In situations where the device 1 is configured to receive a cap 500, the device 1 (such as the spherical embodiment 400 shown in FIG. 2), may include a support 480 (either made from the plurality of pockets 30, or from other structure attached to the device) that supports the cap 500, and may extend outside of the patient during use.

The scaffold 15 may be constructed such that all of the elongate pockets 30 (130, 230) that define the structural walls of the scaffold 15 are fluidly connected, such that a suction (or vacuum force) that is applied to a portion of the scaffold 15 communicates throughout the entire scaffold 15. In other embodiments, the scaffold 15 may be formed from two or more independent fluid zones, wherein each elongate pocket 30 within a single zone is fluidly connected, but multiple zones within a single scaffold 15 are not directly fluidly connected. In embodiments with multiple fluid zones, each fluid zone may be connected to the same vacuum source (shown schematically as 1000) through a common vacuum port 28, or through separate vacuum ports 28 that connect to the vacuum source through a common header (or different vacuum sources 1000). As will be appreciated, embodiments with scaffolds 15 that define multiple fluid zones may be useful for the sake of redundancy, such that a loss of suction (either due to a leak or blockage along a portion of an elongate pocket 30) in one fluid zone (which, as discussed below may cause the scaffold 15 in that zone to lose all or a portion of its rigidity) will not lose suction (rigidity) in the remaining zones.

In some embodiments, the scaffold 15 may be constructed from two thin parallel sheets 42, 44 of flexible material that are aligned in over or next to each other. The two sheets of material 42, 44 (such as polyethylene (Mylar), Nylon, or PVA, or other suitable materials are bonded or heat sealed together along various edges 48*a* to define windows 40, and to define elongate pockets 30 (130, 230), which are defined between two parallel seams 48*a*. The thin sheets 42, 44 may each be about 0.005 to about 0.002 inches thick (inclusive of all thicknesses within this range), or may be a thicker material that is still sufficiently flexible to allow a vacuum to be drawn within the elongate pockets 30, and to accept the desired shape of the device 1. In some embodiments, the first and second sheets 42, 44 may be sealed together throughout the entire area of each window 40, while in other embodiments, the first and second sheets 42, 44 are only sealed together to define each seam 48*a*. Finally, in some embodiments sheets 42, 44 forming the windows 40 within the scaffold 15 may be cut (without cutting the seams 48*a*) to allow for access through the device, such as through a retractor, to access a portion of the viscera outside of the retractor.

In some embodiments, the seams 48*a* are constructed to be substantially air-tight. In some embodiments, an elongate wire or cord 48 may be disposed between the two sheets of material 42, 44 where the seam 48*a* is to be formed. When provided, the wire or cord 48 provides a surface upon which both opposite sheets of material 42, 44 are sealed to prevent any discontinuities in the sealed edge 48*a* (that could leak air therethrough) or to block air flow in situations where small discontinuities in the seal 48 exist. In other embodiments, the two sheets 42, 44 may be sealed directly together along the sealed edge 48*a*.

The pockets 30 (130, 230) may include a volume of foam or other expanded and compressible material that is disposed upon the length of the elongate pocket 30. The compressible material may be a foam, such as an open cell foam formed with a plurality of voids (schematically as 56 in FIG. 3*a*) distributed throughout the volume of the foam. Some suitable materials may be expanded polyethylene, or foams made of other expanded materials. In some embodiments polyester foams may be suitable, such as known "acoustic" foam. In other embodiments, the compressible material may be a plurality of small particles, granules, pellets, ground-material such as bio-compatible expanded foam pellets, coarse-ground coffee, poly vinyl alcohol (PVA) granules, or polymeric regular polyhedrons peanuts, or similar regular or irregular shaped rigid pieces, which will jam against one another when compressed by an overlying film and resist sliding past one another and are relatively light in weight for their given volume.

Figure 3A:
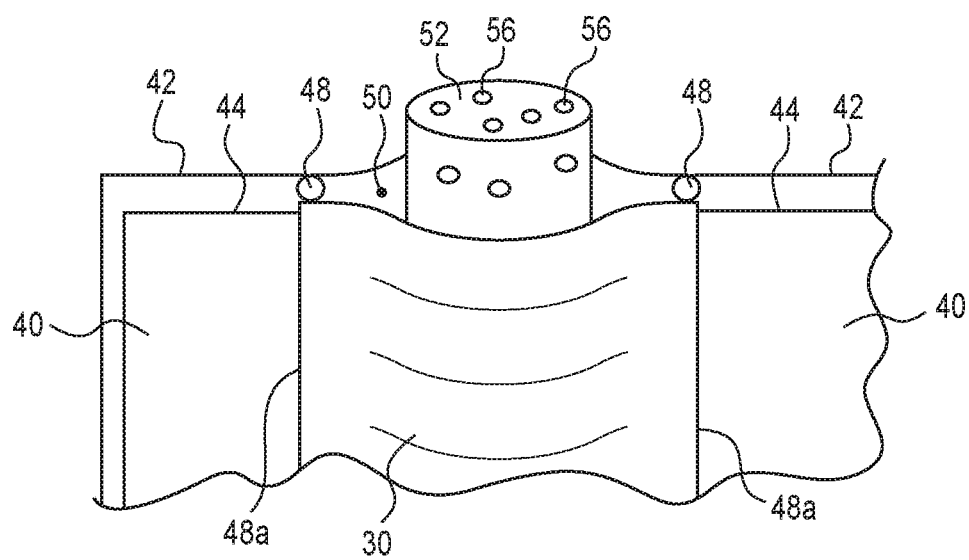
FIG. 3a is a view of a portion of an elongate pocket along section A-A of any one of FIG. 1, 2, or 6 in a normal configuration.
Figure 3B:
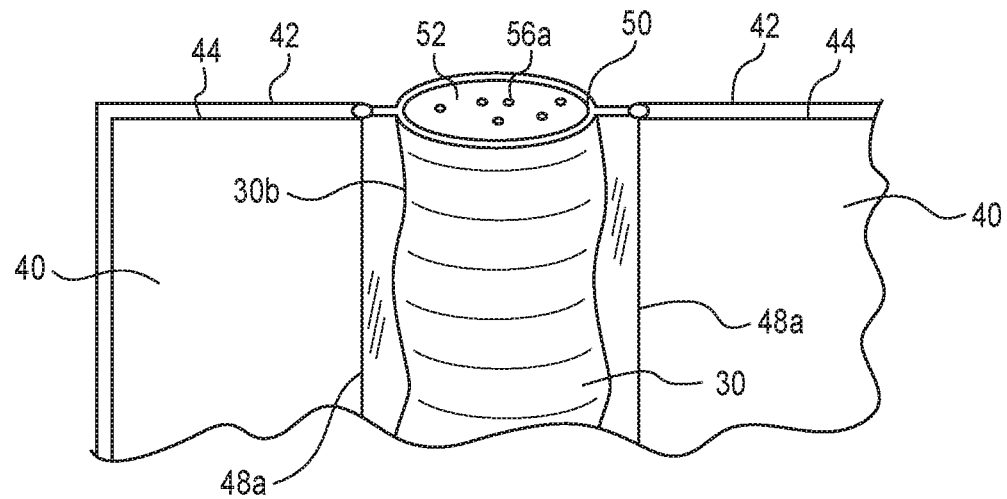
FIG. 3b is the view of FIG. 3a in the influence of a suction force.

A first configuration for an elongate pocket 30 is depicted in FIGS. 3*a* and 3*b*. The pocket 30 is defined by two elongate seams along parallel edges 48*a*, which are formed by bonding or sealing the two sheets of material 42, 44 therealong. The pocket 30 includes an internal volume, which receives one or more cylindrical strips of foam 52 or other type of expanded and collapsible structure (such as foam 52 or other materials) that extends along the length of the pocket 30. The foam 52 may be round in cross-section, or in other embodiments oval, elliptical, arcuate, square, or other thin polygonal shapes in cross-section. As shown schematically in FIG. 3*a*, the foam 52 includes a plurality of voids 56, normally filled with air when the foam 52 is in its normal expanded state, and due to the circular cross-section of the foam 52 with respect to the pocket 30, the pocket includes empty portions 50 between each seal 48*a* and each opposite radial side of the foam 52.

As shown in FIG. 3*a*, the pocket 30 (and therefore the scaffold 15 as a whole) is substantially flexible when in the normal configuration, due to the normal flexibility of the foam 52 and the air within the empty portions 50 of the pocket 30. As shown in FIG. 3*b*, when a suction is drawn within the pocket 30, the plurality of voids 56 in the foam 52 are compressed (as shown schematically as 56*a*) due to the air being withdrawn from within the foam 52, as well as the air withdrawn from the open spaces within the pocket 30. As a result of the air being withdrawn, the walls of the pocket 30 are pushed toward the compressed foam 52 (due to the relatively larger air pressure outside of the pocket 30 than within the pocket 30), and the compressed foam 52 becomes significantly more rigid (due to the collapse of the air gaps 56, which normally are compressed and expanded with the application of only minimal force to the foam 56), which causes the scaffold 15 to also become more rigid. As shown schematically as element 30b, the sheets 42, 44 defining the pocket 30 are pulled together, further increasing the rigidity and potentially changing the cross-section of the foam 52.

Figure 4A:
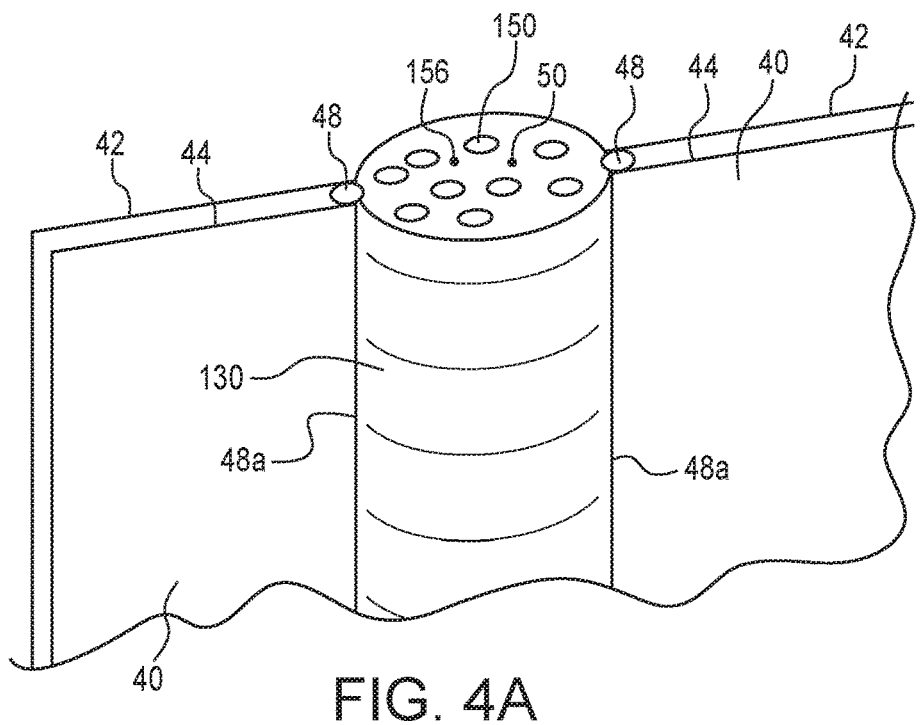
FIG. 4a is a view of another type of elongate pocket along section A-A of any one of FIG. 1, 2, or 6 in a normal configuration.
Figure 4B:
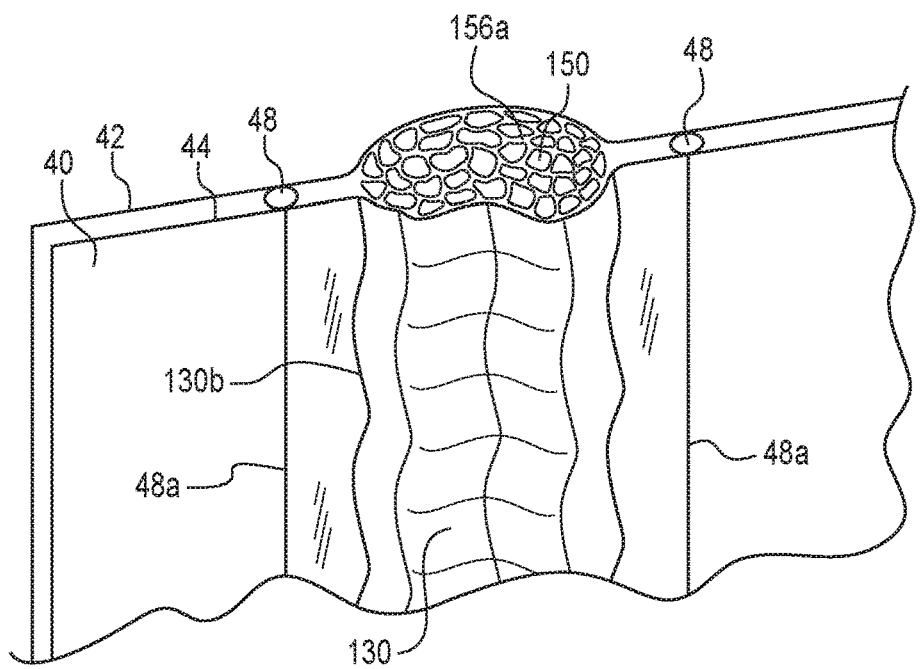
FIG. 4b is the view of FIG. 4a in the influence of a suction force.

Turning now to FIGS. 4a and 4b, another configuration for an elongate pocket 130 is depicted. The pocket 130 that is suitable for construction of a scaffold 15 is schematically depicted, in the normal flexible state (FIG. 4a) and in the rigid state (FIG. 4b) due to the application of suction to the pocket 130. The pocket 130 may be defined between two parallel seams 48a that may be formed as described elsewhere herein. The pocket 130 is full with a plurality of loosely packed pellets 150 peanuts, balls, or other types of small discrete structures of foam or another compressible and flexible material. When resting within the pocket 130 a plurality of spaces are present between neighboring pellets 150, which allow the pocket 130 to be flexible due to the ease of realignment of the plurality of pellets 150 within the pocket 130.

As shown in FIG. 4b, when suction is drawn within the pocket 130, the volume of the pocket 130 is compressed due to the higher relative pressure outside of the pocket 130 than within the pocket 130. Further, in embodiments where the pellets 150 are formed from foam, any voids (not shown, but similar to voids 56 within the foam 52, discussed above) within the foam pellets 150 are compressed due to the air being evacuated from within the pellets 150. The compression of the pellets 150 urges contraction and to more tightly fit together, as further urged together by the reduction of air within the pocket 130. The combination of the increase in rigidity of individual pellets 150 and the overall tighter pack of neighboring pellets 150 (schematically in FIG. 4b as 156a) causes the rigidity within the pocket 130 to increase (which causes the rigidity of the scaffold 15 to increase). As depicted as element 130a, the sheets 42, 44 defining the pocket 130 may be pulled together as shown with element 130b, further increasing the rigidity of the pocket 130.

Figure 5A:
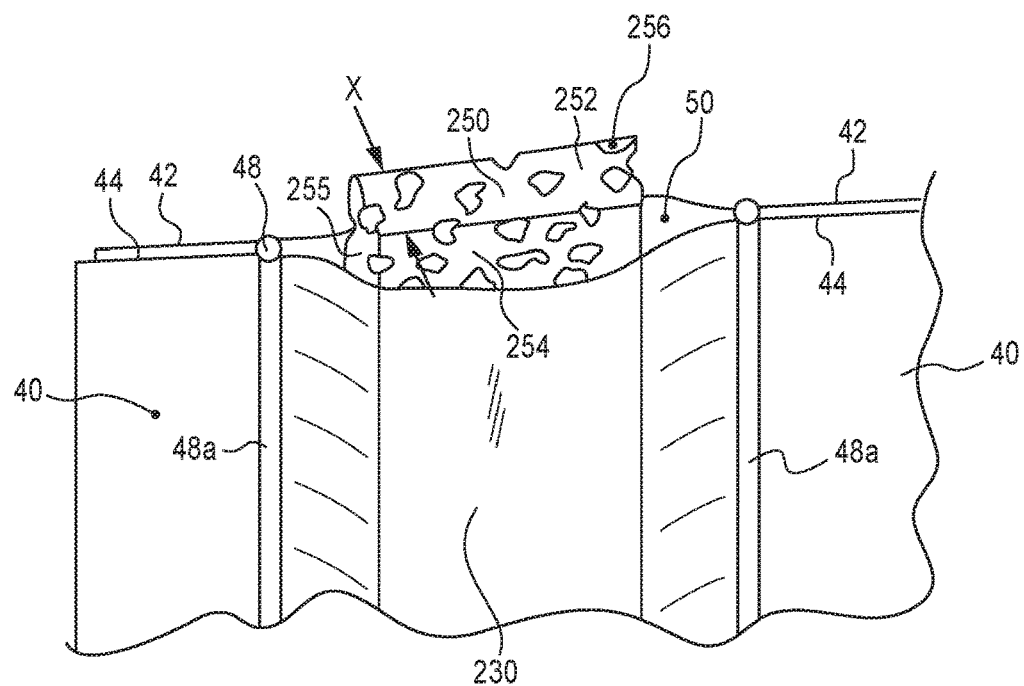
FIG. 5a is a view of another type of elongate pocket along section A-A of any one of FIG. 1, 2, or 6 in a normal configuration.
Figure 5B:
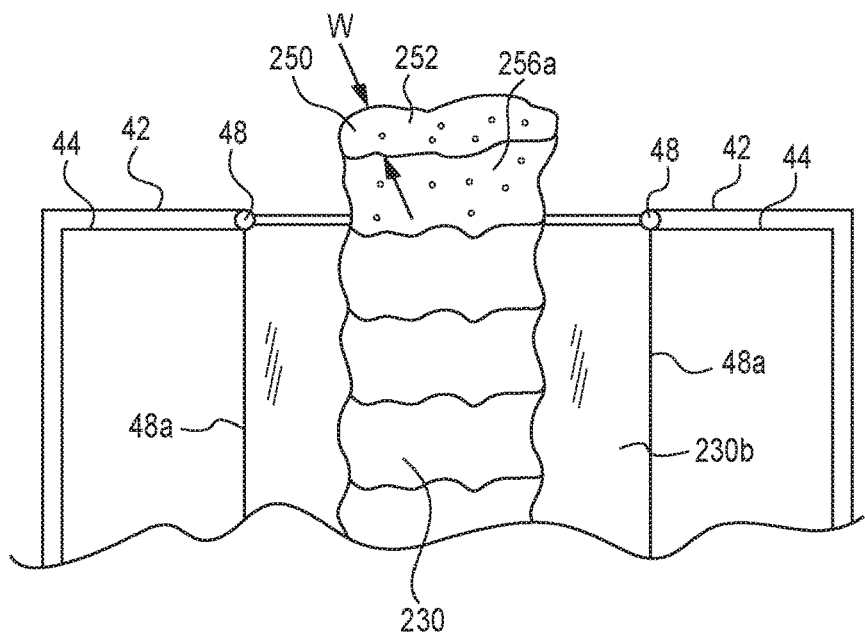
FIG. 5b is the view of FIG. 5a in the influence of a suction force.

Turning now to FIGS. 5a and 5b, another elongate pocket 230 is depicted. The pocket 230 that is suitable for construction of a scaffold 15 is schematically depicted, in the normal flexible state (FIG. 5a) and in the rigid state (FIG. 5b) due to the application of suction to the pocket 230. As with the other pockets discussed above, the pocket 230 may be defined between two parallel seams 48a that may be formed as described elsewhere herein. The pocket 230 receives one or more elongate strips of foam 250 with a rectangular cross-section along its length. As with the foam 52 discussed above, the foam 250 may include a plurality of a voids 256 that are normally filled with air, that allow the expanded foam 250 to be easily expanded. In some embodiments, the foam 250 with the rectangular cross-section may be preferred to provide for increased strength in one direction and decreased strength in the perpendicular direction. For example, in the embodiment shown in FIG. 5a, the wider faces 254 are in parallel with the sheets 42, 44 that define the pocket 230 (and the windows), while the narrower faces 255 are perpendicular to the sheets 42, 44. As can be understood, the pockets 230 in this configuration will be more resistant to bending in a direction parallel with the sheets 42, 44 than a direction perpendicular to the sheets 42, 44 (i.e. into and out of the page displaying FIG. 5a) due to the larger thickness of the foam 250 in the direction parallel with the sheets 42, 44. Placement of the foam 250 in a perpendicular alignment would make the scaffold 15 more resistant to bending into or out of the page upon which FIG. 5a is printed.

As shown in FIG. 5b, when suction is drawn within the pocket 230, the volume within the pocket 230 is compressed due to the higher relative pressure outside the pocket 230 than within the pocket 230. Further, the suction additionally causes the voids 256 within the foam 250 to collapse (as discussed above with respect to voids 56), which compresses the foam 250 and makes the foam 250 more rigid, which ultimately makes the pocket 230 and the scaffold 15 more rigid. Moreover, as shown schematically in FIG. 5b, the collapsing of the voids 256 may cause the foam 250 to establish a non-uniform cross-section, with somewhat arcuate faces, and may cause the width W of the compressed foam (FIG. 5b) to be less than the width X of the expanded foam (FIG. 5a). As shown with element 230 b, the sheets 42, 44 forming the opposite walls of the pocket 230 are pulled together as the air is evacuated out of the pocket 230, further increasing the rigidity of pocket 230.

In some embodiments, the plurality of pockets 30 (130, 230) forming the scaffold 15 may be formed from different constructions within the same scaffold 15, such as portions formed with pockets 30 with portions also formed with pockets 130 and/or pockets 230. As will be appreciated, the use of different pockets with different flexibilities will render a scaffold 15 with specific relatively more or less strong or flexible portions as may be warranted for different design applications. In other embodiments, pockets may be formed with different structures within each pocket, such as, by way of example, the rectangular form 250 and a plurality of pellets 150 disposed outboard of the rectangular foam 250.

Figure 7:
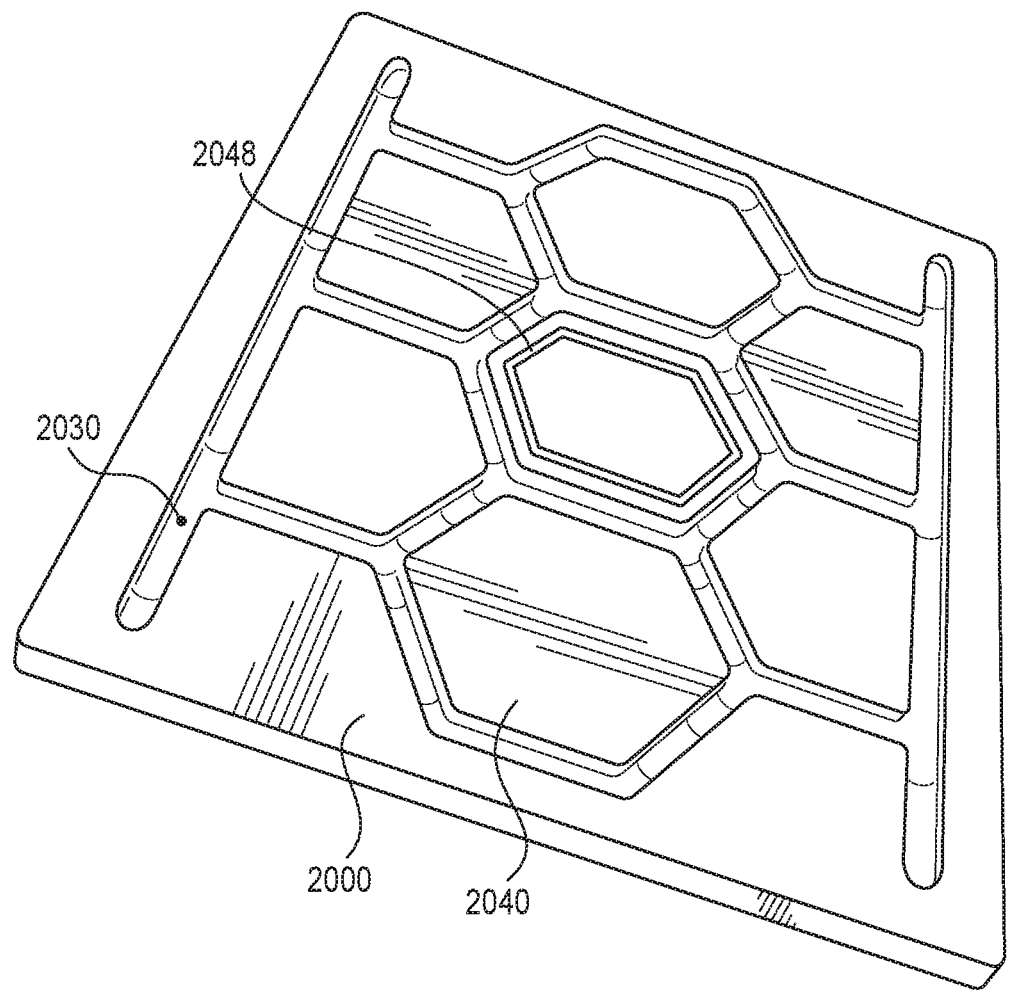
FIG. 7 is a perspective view of a fixture for manufacturing a scaffold for use in a device for selective rigidity.

FIG. 7 depicts a fixture 2000 for forming a scaffold 15. The fixture 2000 may be a flat board that includes a network of tunnels 2030 that are configured in the arrangement where the elongate pockets 30 (130, 230) are desired. The outermost surface of the fixture 2000 may include planar sections 2040 that are disposed where the windows 40 are desired. In some embodiments, the planar sections 2040 of the fixture 2000 may be heated to assist with the formation of the seams 48a, and/or to melt the opposite sheets 42, 44 forming the outer surface of the scaffold 15 together. In some embodiments, the fixture 2000 may include secondary tunnels 2048 that closely surround the tunnels 2030 to provide for placement of the wire or cord 48 to assist in defining the seams 48. As can easily be appreciated, to construct a scaffold, a first sheet 42 may be disposed upon the fixture 2000 and then the material (foam 52, pellets, foam 250, or a combination of these) is placed within the tunnels 2030 on top of the first sheet 42. A second sheet 44 is then placed on the fixture 2000 on the first sheet 42. The seams 48a may then be formed by an external tool, or in other embodiments, a second fixture 2000 contacts the second sheet 44 compressively and may form the seal 48a upon the application of heat. Upon formation of the scaffold 15, the scaffold 15 may then be fixed into the desired shape or orientation, and the vacuum line 28 attached to the pocket 30 to provide communication of suction from the vacuum line 28 to the pockets 30.

As discussed elsewhere herein and specifically depicted in FIGS. 22-25, In some embodiments, the scaffold 15 (including the various embodiments depicted in FIGS. 1-7 and discussed herein) may be constructed from two thin parallel sheets 42, 44 of flexible material that are aligned in over or next to each other. One or both of the sheets 42, 44 may be constructed with a first, inner layer 42a, 44a that is entirely (or has one or more portions that are) sticky, such as having a high friction, a releasable adhesive, or tacky, or low lubricity, or a combination of each of these attributes. The outer surfaces 42b, 44b of one or both of the sheets 42, 44 may be lubricious, or low friction, and/or bio-friendly to minimize the engagement between the sheets 42, 44 and the portions of the anatomy in contact with the scaffold 15.

Figure 23:
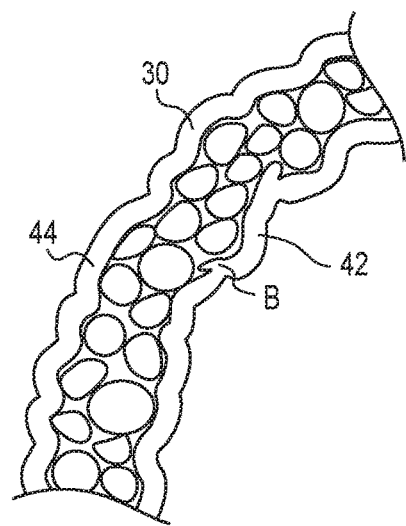
FIG. 23 is the sectional view of FIG. 22 under the influence of a suction force.
Figure 24:
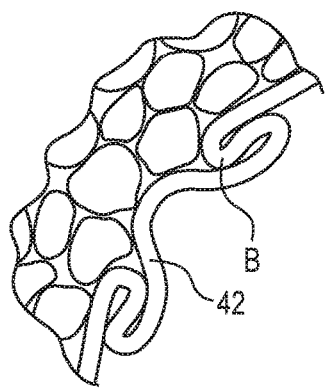
FIG. 24 is another sectional view of FIG. 22 under the influence of a suction force.
Figure 25:
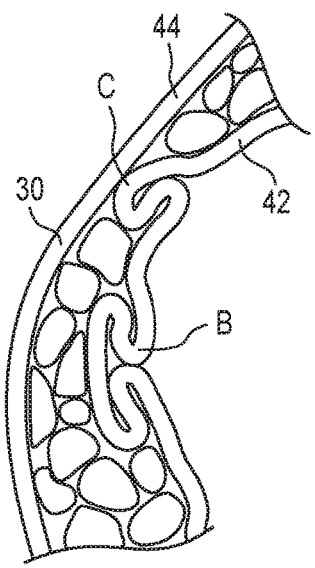
FIG. 25 is another sectional view of FIG. 22 under the influence of a suction force.

As shown schematically in FIGS. 23-25, when the pocket (e.g. 30, 130, 230) is under the influence of the suction or vacuum force, the structures within the pocket tend to collapse and/or align with respect to each other, which increases the density of the pocket and the rigidity of the pocket. When the material within the pocket (such as foam, pellets, granules or the like) decreases in size (collectively and in some embodiments individually) the surface area of the collective and/or individual material decreases and the portions of the sheets 42, 44 defining the pockets tend to overlap, or bunch, or fold upon itself (as depicted with element B in FIGS. 23-25). In embodiments where the inner layers 42a, 44a of the sheets are sticky (or otherwise as discussed above) the overlapping or bunched portions of the sheets stick together in the overlapped, bunched, or folded manner, which has been experimentally been determined to increase the overall rigidity of the pocket. In some embodiments, the inner surfaces 42a, 44a of the first and second layers 42, 44 may stick directly together (FIG. 25, C) which has also been determined to increase local rigidity. In some embodiments, when the vacuum force is released from the pocket, the material therewithin is urged to expand (individually) which decreases the individual and/or collective density of the pocket. As the pocket density decreases, the mated sticky portions 42a, 44a of the first and second layers 42, 44 tend to release, which allows further decrease in the overall density of the pocket.

Turning now to FIGS. 8-21 an elongate device 3000 that is configured to maintain a selective rigidity is provided. The elongate device 3000 may be a catheter or a sheath, such as an access sheath, or another elongate device that is configured where either a partial length of a working portion of the device, or in other embodiments, a total length of the working portion of the device is nominally at a first diameter, and with an expandable portion 3001 is capable of being radially expanded (such as with a balloon 3610 disposed within a lumen 3020 of the device, as discussed in detail below), and that is capable of retaining the expanded diameter when the radial expansion force is released. One of ordinary skill in the art after a thorough review of this specification and figures will contemplate that the device 3000 may be usable for a variety of clinical applications, and specifically clinical applications where it is necessary to increase a radial diameter of a portion of a device at a remote location within a patient, and to retain the increased radial diameter while allowing access through the lumen of the device. Such clinical applications may be an access sheath (urological, vascular, endoscopic or the like), a delivery system, an indwelling catheter, and the like.

Figure 8:
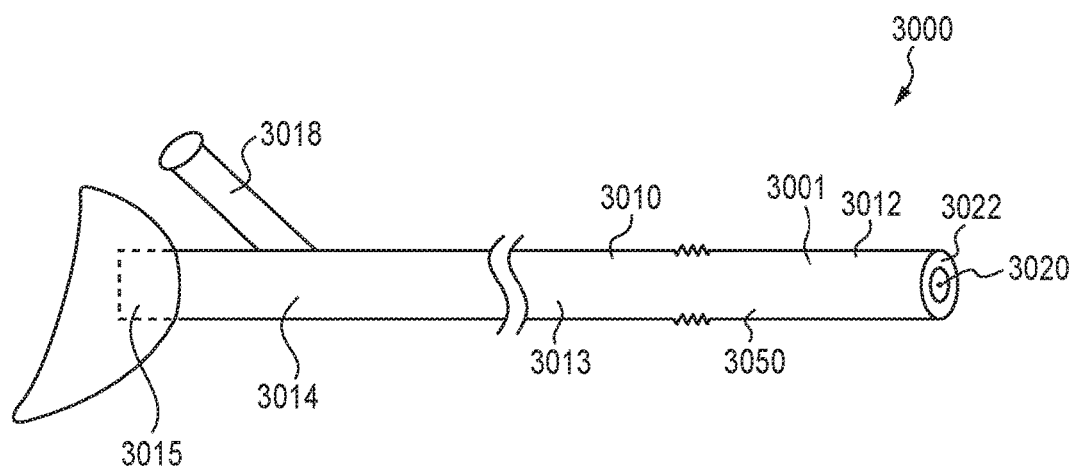
FIG. 8 is a perspective view of a medical device with an expandable portion that may be maintained in an expanded configuration, depicting the expandable portion in a nominal, unexpanded configuration.
Figure 9:
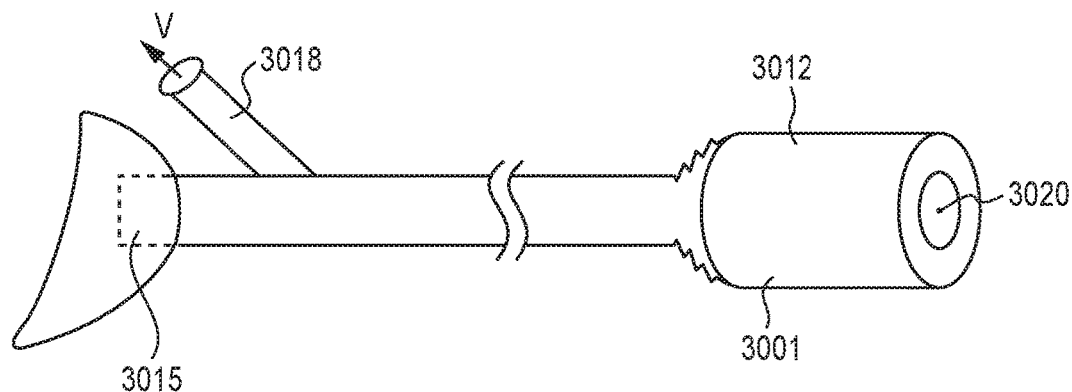
FIG. 9 is the view of FIG. 8 with the expandable portion in an expanded configuration.

As shown in FIGS. 8 and 9, the medical device 3000 extends between a distal end portion 3012 and a proximal end portion 3014 with a central portion 3013 disposed therebetween. The distal and central portions 3012 are 3013 may be configured to be inserted within the anatomy of a patient (mammal or human, or other patients with an anatomy that might favorably be used with the medical device 3000), with the proximal end portion 3014 retained outside of the patient to be manipulated by the medical professional. While the medical device 3000 is depicted and described with a radially expandable portion 3001 upon the distal end portion 3012 of the medical device 3000, the expandable portion 3001 could be provided at a position proximal of the distal tip 3022 of the device 3000 such as upon the central portion 3013 of the device 3000. One of ordinary skill in the art with a thorough review of this specification would readily understand how the device 3000 could be readily modified to locate one or more expandable portions 3001 at differing locations upon the device 3000 than specifically described and depicted herein.

In some embodiments, the device 3000 may include multiple expandable portions 3001 that are disposed in series upon the device 3000, with a single vacuum lumen 3040 (discussed below) in communication with each expandable portion 3001, or in other embodiments with a dedicated vacuum lumen 3040, 3040a for each expandable portion 3001.

In some embodiments, the expandable portion 3001 may be configured to be expandable around the entire circumference of the device 3000, while in other embodiments, the expandable portion(s) 3001 may be configured to only be expandable about one or more portions (such as half of the circumference, one quarter of the circumference, and the like) of the circumference of the device 3000.

In some embodiments, the retention members 3002 (see e.g. FIGS. 10-11, 18-20) (such as the plurality of particles 3080 or the collapsible foam 3180, each discussed below) may be provided around the entire geometry (length and/or circumference) of the expandable portion 3001, while in other embodiments, the retention members 3002 may only be disposed upon a portion of the expandable portion 3001 less than the entire expandable portion 3001 such that only a predetermined portion of the expandable portion 3001 is retained in the expanded configuration when the radial expansion force is released.

The medical device 3000 may include a first lumen 3020 that extends between and through the distal and proximal end portions 3012, 3014 (and the central portion 3013 therebetween and out of the distal tip 3022, when provided) and allows for extending an elongate device therethrough, for completing a clinical task associated with the device 3000 (such as for example passing a basket therethrough, or delivering a device such as a stent therethrough), and allows for receiving and/or translating a balloon catheter 3600 (FIGS. 12, 13, 21, or another elongate expandable member) therewithin so that a balloon 3610 of the balloon catheter 3600 is disposed within the expandable portion 3001 to urge the expandable portion 3001 to radially expand outward when the balloon 3610 is inflated.

The proximal end portion 3014 may include an opening and/or a fitting 3015 (shown schematically in FIGS. 8, 9) (such as a luer fitting) to allow an elongate device to be passed into the first lumen 3020 through a proximal opening 3015. The proximal end portion 3014 may additionally include a vacuum port 3018 that provides for fluid communication with the vacuum lumen 3040 (or vacuum lumens 3040, 3040a).

As shown in FIG. 8, the expandable portion 3001 may normally rest at the same outer diameter and/or outer shape as the central portion 3013 and/or any remaining length of the distal end portion 3012 that does not include the expandable portion 3001. As shown in FIG. 9, the expandable portion 3001 may be radially expanded (all or a circumferential portion thereof) to a larger diameter, which increases the diameter of the first lumen 3020 and expands the outer surface of the distal end portion 3012 radially outward.

Figure 10:
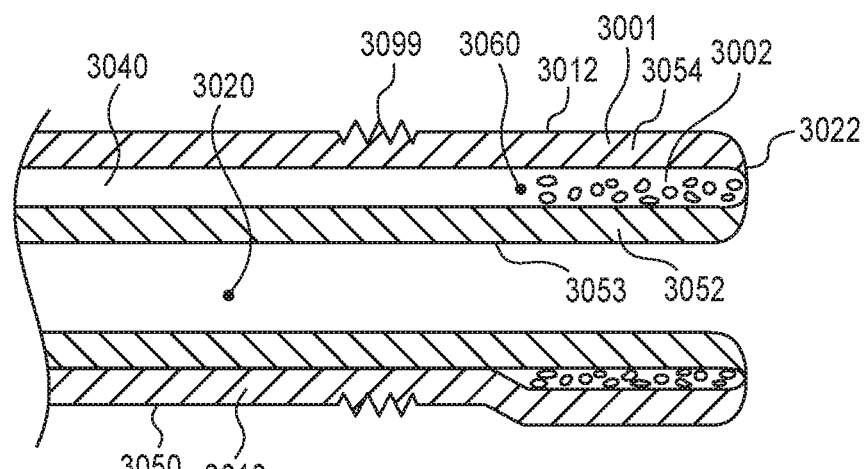
FIG. 10 is a cross-sectional view of the distal and central portions of the device of FIG. 8.
Figure 11:
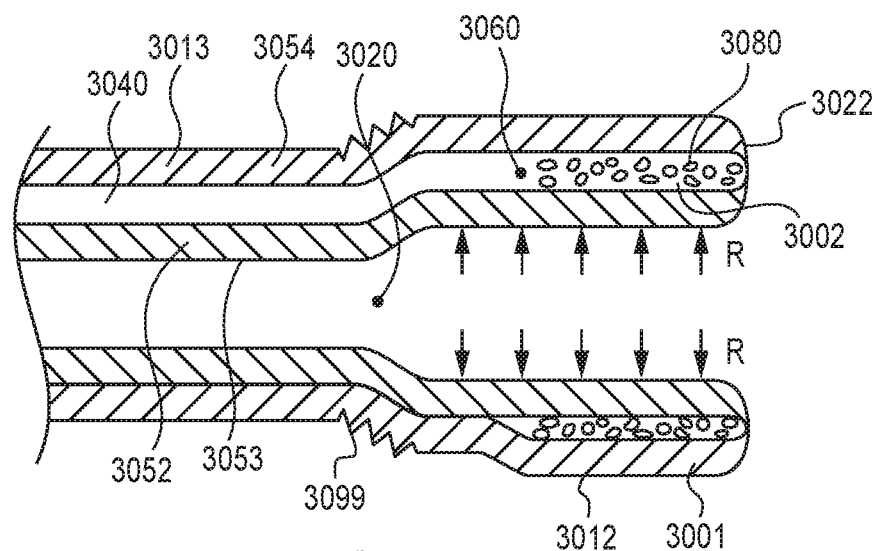
FIG. 11 is a cross-sectional view of the distal and central portions of the device of FIG. 9.
Figure 12:
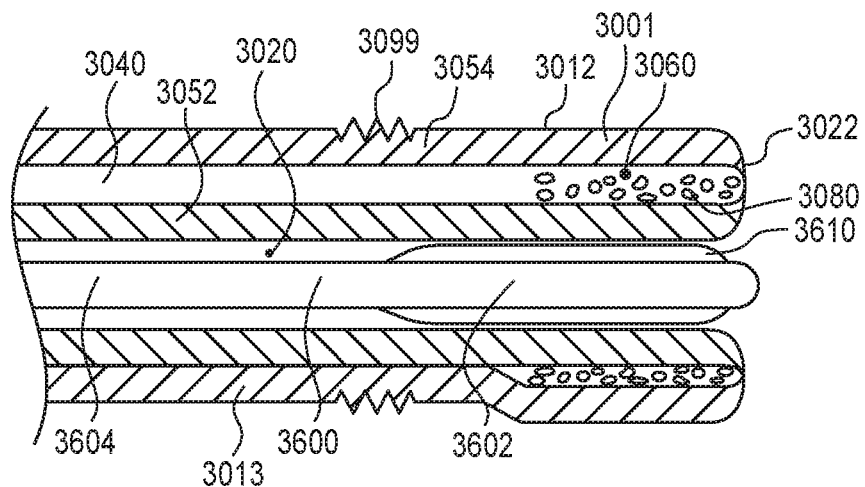
FIG. 12 is the view of FIG. 10 with a balloon disposed within the first lumen in registry with the expandable portion.
Figure 13:
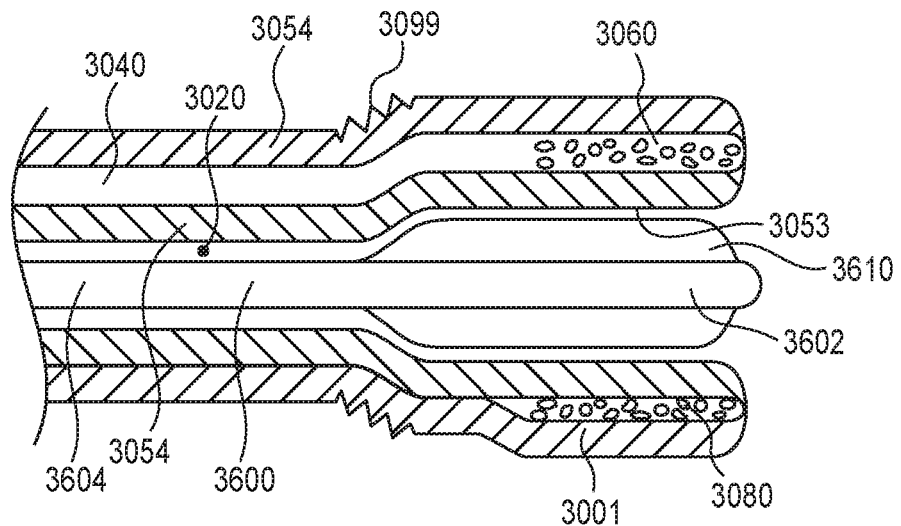
FIG. 13 is the view of FIG. 12 with the balloon expanded.

FIGS. 10-11 depict cross-sectional views of FIGS. 8 and 9, respectively, with FIG. 11 depicting the distal end portion 3012 expanded due to a radial force R applied to the inner surface 3053 of the first lumen 3020. As understood with reference to FIGS. 10-11, the application of an outward radial force R upon the distal end portion 3012 causes the portions of the distal end portion 3012 receiving the radial force R to expand radially outward, while the central portion 3013 remains at its normal diameter. In some embodiments, a stress relief 3099 may be provided upon the wall 3050 of the device 3000 to provide a discontinuity between the expandable portion 3001 and the neighboring portion upon the device, such as the central portion 3013 or a remaining portion of the distal end portion 3012 when the expandable portion 3001 is expanded. In other embodiments where the expandable portion 3001 is only upon a part of the distal end portion 3012, or upon a different location upon the device 3000, one or more stress reliefs 3099 may be provided at desired positions upon the device 3000 to facilitate relative expansion of the desired expandable portions only.

The vacuum, or second, lumen 3040 may extend from the proximal end portion 3014 (and the port 3018) to the expandable portion 3001 and specifically to an interface 3060 between the first and second layers 3052, 3054 of the wall 3050 to allow for selective fluid (vacuum) communication with the interface 3060 to allow for selective transfer of a vacuum, or suction, force V to the interface 3060. As shown in FIGS. 11, 12, 14, and 15, the vacuum lumen 3040 may remain open to allow for vacuum force to be transferred therethrough when the expandable portion 3001 is in the nominal configuration and when the expandable portion 3001 is expanded radially outward to allow the vacuum force V to be continuously transmitted to the interface 3060 when the expandable portion 3001 is expanded, which retains the expandable portion 3001 in the expanded configuration.

The wall 3050 of the device 3000 may include first and second layers 3052, 3054 that are concentrically aligned to define each of the distal, central (when provided) and proximal end portions 3012, 3013, 3014. The first layer 3052 may define the inner surface 3053 of the first lumen 3020. In some embodiments, the first layer 3052 may have a discrete thickness (forming a first surface that defines the first lumen 3020, an inner wall thickness, and a second, upper surface) while in other embodiments, the first layer 3052 may be a film with opposite first and second surfaces and a negligible thickness. Similarly, in some embodiments the second layer 3054 may have a discrete thickness (forming a first surface that defines the outer surface of the device 3000, a wall thickness, and a second, inner surface) while in other embodiments, the first layer 3052 may be a film with opposite first and second surfaces and a negligible thickness. As shown in FIGS. 10 and 11, along the distal end portion 3012, and specifically the expandable portion 3001, the first and second layers 3052, 3054 each contact opposite sides of the interface 3060, while in the remaining length of the device 3000, the first and second layers 3052, 3054 contact each other (except in locations where the vacuum lumen 3040 may be disposed between the first and second layers 3052, 3054 (FIG. 10)).

The first and second layers 3052, 3054 may be sealed at the distal end of the interface 3060 and distally of the interface 3060 to the distal tip 3022 of the device 3000, and the seal may extend around the entire circumference of the device. In embodiments where the expandable portion 3001 is less than the circumference of the device 3000, the seal exists at the end of the distal end of the interface 3060 where the interface 3060 exists and elsewhere as needed for integrity. In embodiments where the expandable portion 3001 is disposed at or proximate to the distal tip 3022, the first and second layers 3052, 3054 are sealed to define the distal tip 3022.

In some embodiments, the portions of the first and second layers 3052, 3054 that define the interface 3060 may be sticky, such as having a high friction, a releasable adhesive, or tacky, or low lubricity, or a combination of each of these attributes (and similar to the depictions in FIGS. 22-25). As with the embodiments of the pockets with the sticky inner surfaces 42a, 44a of the pockets discussed above, when the interface 3060 is under the vacuum force V, the retention member 3002 reaches a smaller volume (collectively and/or individually) and the inner surfaces of the first and second layers 3052, 3054 may have excess surface that forms the interface 3060 that is floppy or wavy, i.e. not directly enclosing the retention member 3002. These portions may stick to each other, or to the opposite layer, which may increase the overall rigidity of the interface 3060 within the expandable portion 3001 (each discussed elsewhere herein). The sticky surfaces may be configured such that they release from each other when the vacuum force V is released and the retention member 3002 is allowed to return to its normal state.

In other embodiments, additional layers or coatings may be provided upon the device 3000 for strength, observation (such as a layer with a portion that can be indirectly visualized, such as an echogenic or radiopaque portion), lubricity, friction, hydrophobic, hydrophilic, or other properties or design purposes in addition to the first and second layers as understood by one of skill in the art. One of ordinary skill with a thorough review of this specification will understand how to add these types of other features/structures to the device 300 while maintain the benefits of the structure of the device 3000 disclosed herein. In some embodiments, at least the central and proximal end portions 3013 and 3014, and a portion of the distal end portion 3012 without an expanding portion 3001 may be formed from a single layer, i.e. from a single material along the wall thickness, with two layers provided surrounding the interface 3060.

The interface 3060 is disposed within the expandable portion 3001 and encloses a retention member 3002, or a plurality of retention members 3002, such as a plurality of particles 3080, or a compressible form 3180, or another structure that is configured to be able to be expanded or otherwise deformed, and is also configured to either rearrange with respect to each other (i.e. plurality of particles 3080) or to collapse upon itself (i.e. foam 3180) under the force of a vacuum or negative pressure communicated with the interface 3060. The voids or air pockets within the interface 3060 additionally tend to collapse (with the first and second layers 3052, 3054 defining the interface 3060 tending to be drawn toward each other under the influence of the vacuum force v.

The interface 3060 may be disposed within the expandable portion 3001 around the entire circumference of the expandable portion 3001, or as mentioned above the interface 3060 may be disposed about only one or more portions of the circumference of the device 3000. The interface 3060 is in fluid communication with the vacuum lumen(s) 3040 and ultimately with the vacuum port 3018, to allow a vacuum force drawn at the vacuum port 3018 to be communicated to the interface 3060.

In embodiments where the retention member is a plurality of particles 3080 (FIGS. 10-17), the particles 3080 are normally disposed freely within the interface 3060 to readily allow for expansion or deformation of the expandable portion 3001. The plurality of particles 3080 may be of either uniform geometry or may be non-uniform geometry. The plurality of particles 3080 are preferably of a geometry that is configured to closely align with respect to other particles 3080 to allow for tight packing within the interface 3060 and minimize the space therebetween, which increases the rigidity of the combined plurality of particles 3080. In some embodiments, the particles 3080 may be uniform or non-uniform spheres, bricks, or non-uniform shapes with voids and indentations. The plurality of particles 3080 may be relatively light with a relatively low density such that the plurality of particles 3080 easily move within the interface 3060 and in the presence of a vacuum (V, FIGS. 9, 14) are drawn toward each other under the influence of the vacuum force V from the vacuum lumen 3040. In some embodiments, each of the plurality of particles 3080 may be substantially rigid such that the aligned particles 3080 (under the vacuum force V) tend to maintain their collective shape if the vacuum force V is maintained. Alternatively, the particles may be compressible to increase the density of the collective particles under the force of the vacuum V within the interface 3060.

The particles 3080 may be small pellets of foam, such as open cell foam formed with a plurality of voids distributed throughout each particle the foam. Some suitable materials may be expanded polyethylene, or foams made of other expanded materials. In some embodiments polyester foams may be suitable, such as known "acoustic" foam. In other embodiments, the particles 3080 may be granules, pellets, ground-material such as bio-compatible expanded foam pellets, coarse-ground coffee, poly vinyl alcohol (PVA) granules, or polymeric regular polyhedrons peanuts, or similar regular or irregular shaped rigid (or compressible) pieces, which will jam against one another when compressed by an overlying film or first and second layer 3052, 3054 and resist sliding past one another and are relatively light in weight for their given volume.

In still other embodiments, the particles 3080 may be particle jamming beads. In some embodiments, the particles 3080 may be brick shaped with a major dimension larger than the other two mutually perpendicular dimensions. In other embodiments, the particles 3080 may be cubes. In other embodiments, the particles 3080 may be a sphere, or other arcuate bodies, such as an ovoid. In still other embodiments, the particles may be a pyramid (truncated or not), or a cone (truncated or not). In other embodiments, the particles 3080 may be a step (e.g. a rectangle with a cube disposed upon one end of the rectangle with parallel side and end surfaces), or a cylinder. In some embodiments, the particles 3080 may be irregular and formed with one or more projections and/or one or more indentations. In some embodiments, a combination of two or more of the above shapes may be provided, or the particles may be uniform, in size and/or shape, or may have varying sizes and/or shapes. One or ordinary skill, with a thorough review and understanding of this disclosure, will be able to select the appropriate size(s) and shape(s) of the plurality of particles 3080 to allow for a loose interface 3060 when at or above atmospheric pressure, and a tightly packed, more dense interface 3060 when under the influence of a vacuum force v from the vacuum lumen(s) 3040.

The particles 3040 may be relatively small, i.e. on the order of one eighth French, one sixth French, one quarter French, one third French, one half French (in diameter or along a major or minor dimension), or smaller, such that the overall width of the interface 3060 is minimized both when the interface is at atmospheric pressure (or above) and when the particles 3080 are organized under the vacuum force V.

Figure 18:
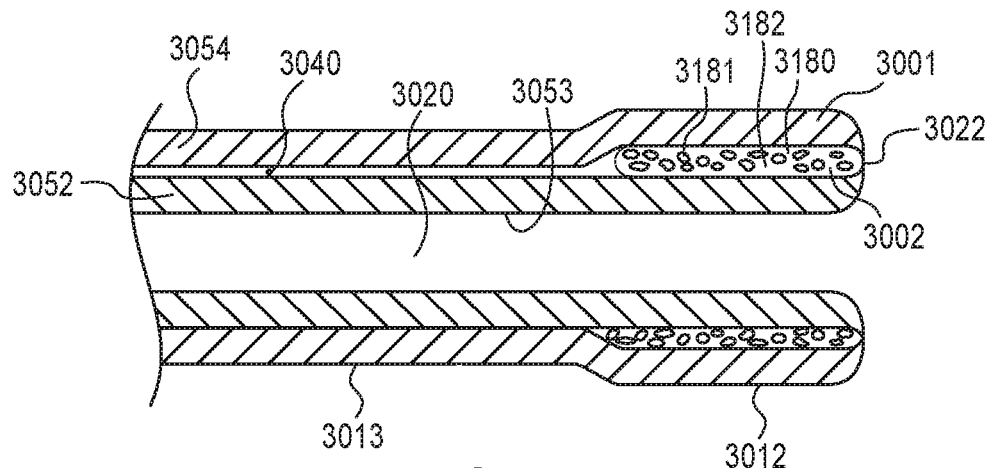
FIG. 18 is a cross-sectional view of another embodiment of the medical device with an expandable portion that may be maintained in an expanded configuration.
Figure 19:
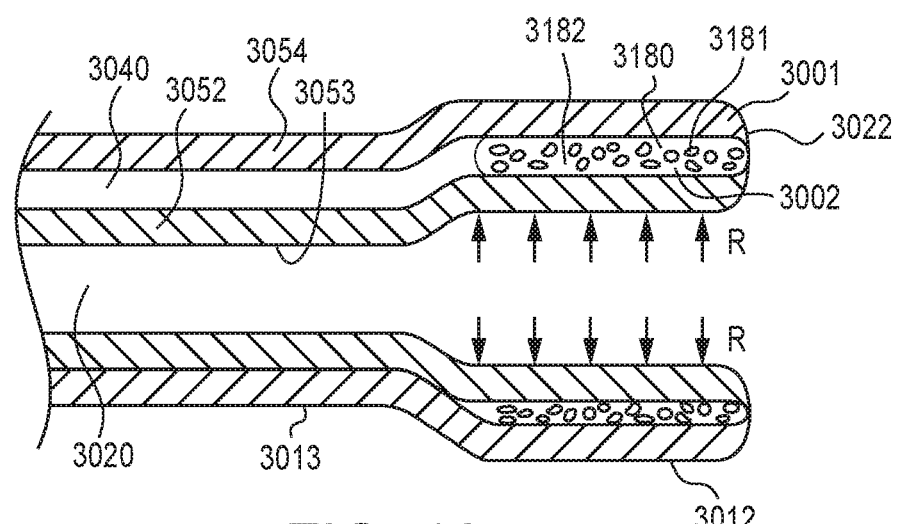
FIG. 19 is the view of FIG. 18 with the expandable portion in the expanded configuration.
Figure 20:
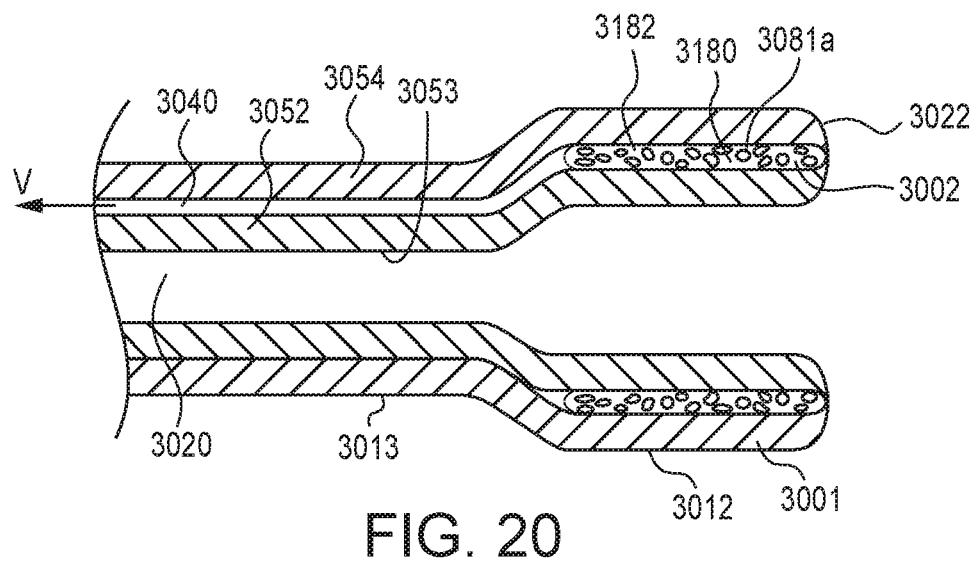
FIG. 20 is the view of FIG. 19 showing schematically a vacuum force applied to the vacuum lumen and the interface.
Figure 21:
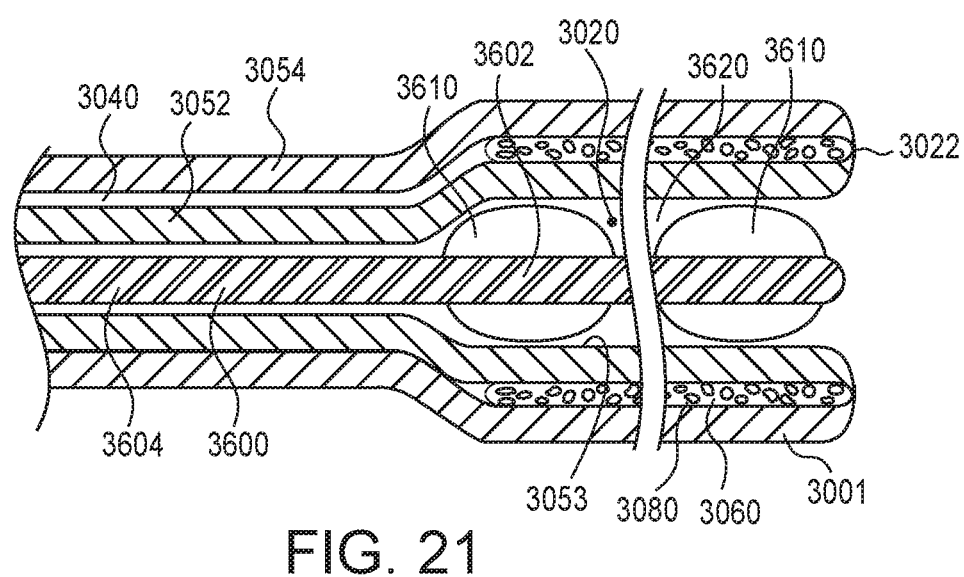
FIG. 21 is a cross-sectional view of another embodiment of the medical device with an expandable portion that may be maintained in an expanded configuration, showing the expandable portion in an expanded configuration.
Figure 22:
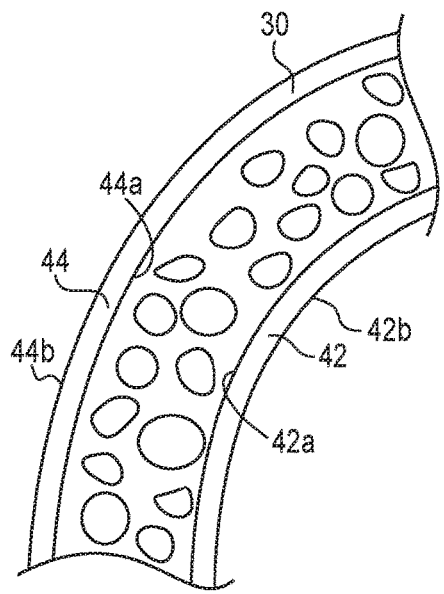
FIG. 22 is a sectional view of a portion of a pocket associated with the device of FIG. 1 (and capable of being provided with the device of FIG. 8).

In other embodiments, shown in FIGS. 18-20, the interface 3060 may house a compressible foam 3180 that is nominally at a first thickness (FIG. 18, 19) when the interface 3060 is at atmospheric or positive pressure, and compresses when the interface 3060 is at a vacuum. The foam may be an open cell foam with a plurality of voids 3181 (FIG. 19) disposed within a "solid" foam material 3182 (FIG. 19). The voids compress 3181a (FIG. 20) when the interface 3060 (and therefore the foam 3180) is in the presence of a vacuum force V, which causes the overall thickness of the foam 3180 to be reduced, and the rigidity of the foam 3180 to increase under the vacuum force V (FIG. 20).

As discussed herein, the expandable portion 3001 may be expanded radially outward with the expansion of balloon 3610 disposed upon a balloon catheter 3600 that extends through the first lumen of the device 3000, which provides a radial force R upon the inner surface 3053 of the lumen 3020 within the expandable portion 3001. In some embodiments shown in FIG. 21, the balloon catheter 3600 may include two or more spaced balloons 3610 disposed in series with a longitudinal space 3620 disposed therebetween. The balloons 3610 may each fluidly communicate with the same inflation lumen (not shown) in the balloon catheter 3600 such that each balloon 3610 inflates and compresses together, while in other embodiments, each balloon 3610 may fluidly communicate with a dedicated lumen to allow for selective inflation and compression as desired. The balloon catheter 3600 may include a second portion 3604 that may be proximal or distal of the balloon 3600, depending upon the placement of the expandable portion 3001 within the device 3000.

Figure 14:
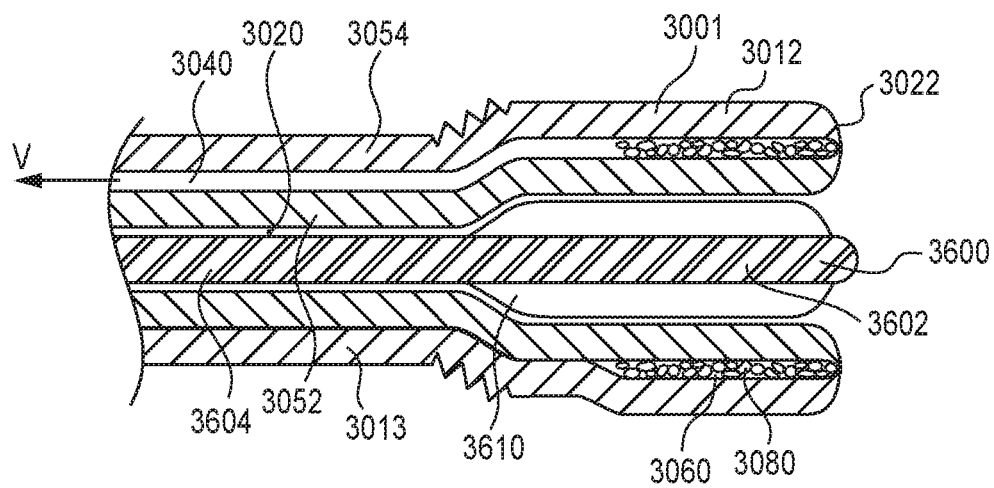
FIG. 14 is the view of FIG. 13 showing schematically a vacuum force applied to the vacuum lumen and the interface.
Figure 15:
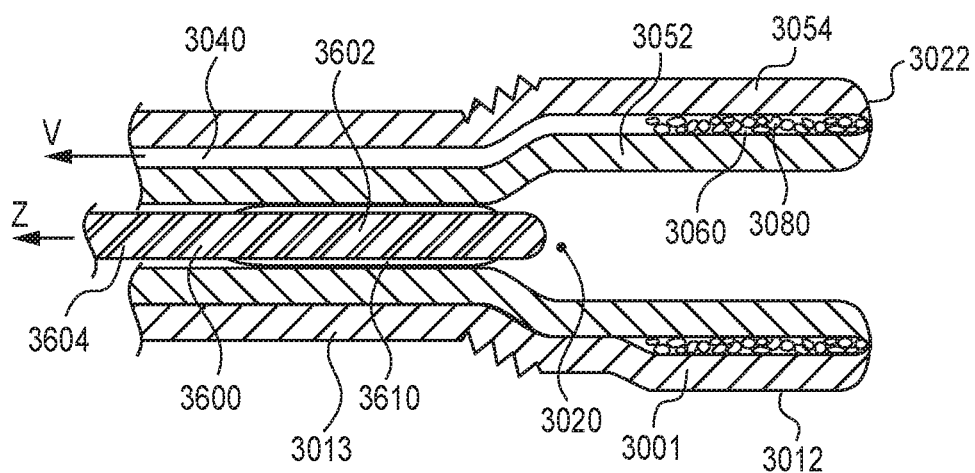
FIG. 15 is the view of FIG. 14 with the balloon collapsed and withdrawn from registry with the expandable portion.

As shown schematically in FIGS. 14 and 15, the interface 3060 may receive a vacuum force V when in an expanded configuration, with the interface 3060 (and remainder of the expandable portion 3001) being expanded by a balloon 3610 disposed within the first lumen 3020 in registry with the expandable portion 3001. As discussed elsewhere herein, the interface 3060, and specifically the retention member(s) 3002 is configured to retain the expanded configuration under a vacuum force V applied thereto through the vacuum lumen 3040, such that the expandable portion 3001 remains expanded when the balloon 3610 is collapsed and the balloon catheter 3600 is withdrawn (in the direction Z, FIG. 15) with the vacuum force V retained.

Figure 16:
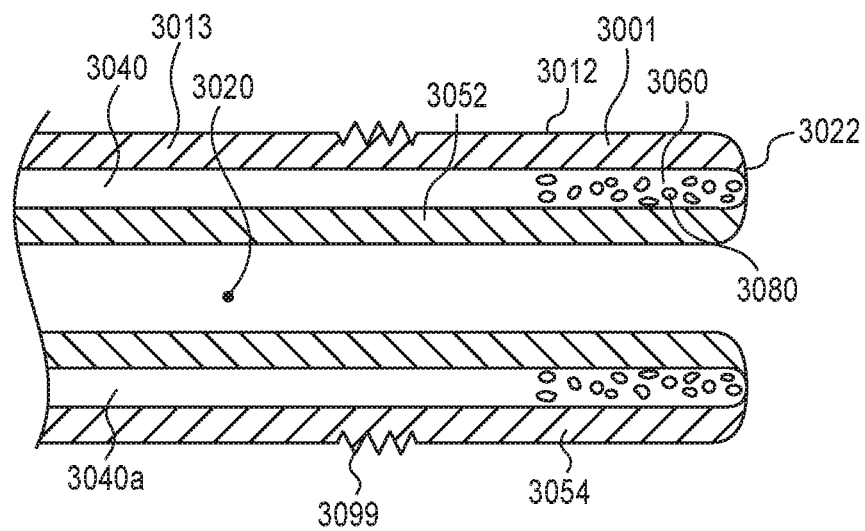
FIG. 16 is a cross-sectional view of another embodiment of the medical device with an expandable portion that may be maintained in an expanded configuration.
Figure 17:
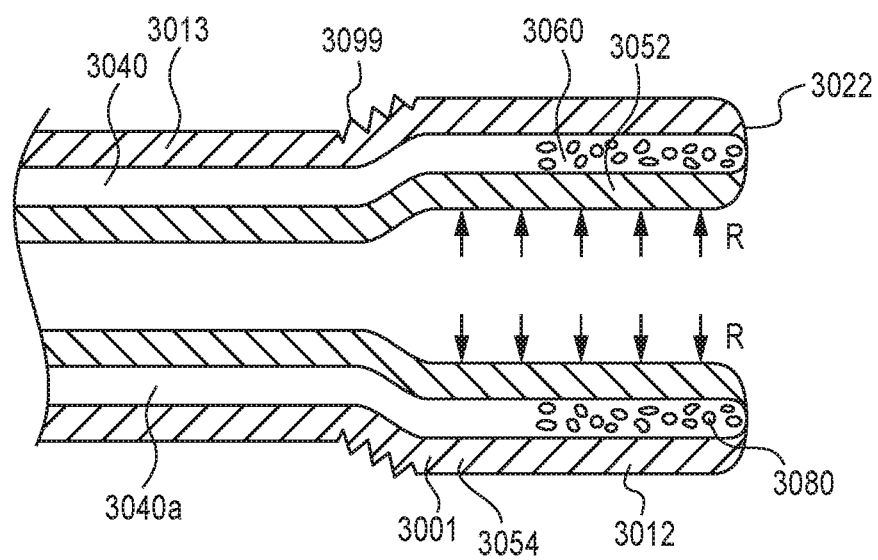
FIG. 17 is the view of FIG. 16, with the expandable portion in an expanded configuration.

In some embodiments shown in FIGS. 16 and 17, multiple independent vacuum lumens 3040, 3040a may be provided, which each provide for fluid communication with the interface 3060 to selectively and/or in parallel apply the vacuum force V to the interface 3060. The use of multiple independent vacuum lumens 3040, 3040a may be beneficial to maintain a vacuum force V if one of the multiple vacuum lumens becomes collapsed or blocked or otherwise prevents or minimizes the vacuum force V provided to the interface 3060. In other embodiments, multiple interfaces 3060 (each filled with a retention material 3002, as discussed elsewhere herein) may be provided in series along the length of the device 3000 are respectively disposed within multiple expandable portions 3001. In these embodiments, multiple vacuum lumens 3040, 3040a may be provided to allow for each interface 3060 to be independently presented with a vacuum force V (from independent or the same vacuum source connected to one or multiple vacuum ports 3018). In other embodiments, each interface 3060 may be fluidly connected to the same vacuum lumen 3040.

While the preferred embodiments of the disclosed have been described, it should be understood that the invention is not so limited and modifications may be made without departing from the disclosure. The scope of the disclosure is defined by the appended claims, and all devices that come within the meaning of the claims, either literally or by equivalence, are intended to be embraced therein.

The invention claimed is:

1. An expandable and compressible medical device for obtaining selective rigidity with respect to a patient, comprising:
   an elongate flexible catheter that extends between a distal end portion and a proximal end portion with a first lumen disposed through the catheter, and a second lumen that extends through a catheter wall into the distal end portion, wherein the distal end portion of the catheter wall is an expandable portion;
   the catheter wall comprises a first layer that defines an inner surface of the first lumen and a second layer disposed radially outside of the first layer, and wherein the first and second layers are sealed together proximate to a distal tip of the catheter, and an interface is established between the first and second layers, wherein the interface is established within a volume bounded by the first layer, the second layer, and locations where the first and second layers are sealed together, the interface is located within the expandable portion of the catheter wall; and
   further comprising a retention member disposed within the interface between the first and second layers within the distal end portion, and wherein the second lumen is fluidly connected with the interface,
   wherein the retention member is configured to be aligned in a dense configuration under an influence of a vacuum force applied to the interface via the second lumen, wherein the retention member is biased to expand to a less dense configuration when the interface is at atmospheric pressure,
   wherein at least a portion of a surface of one or both of the first and second layers that establish the interface is a sticky portion, and the sticky portion is configured to releasably stick to other portions of the interface under the influence of the vacuum force.

2. The medical device of claim 1, wherein the first and second layers are each formed from a common tube.

3. The medical device of claim 1, wherein the first and second layers are radially expandable when urged outwardly by a radial force, wherein the radial force is imparted upon the inner surface of the first layer from within the first lumen.

4. The medical device of claim 1, wherein the second lumen is configured to maintain fluid communication with the interface when the first and second layers are in a radially expanded configuration.

5. The medical device of claim 1, wherein the retention member comprises a plurality of particles that are collectively disposed within the interface, the plurality of particles are configured to pack tightly with one another and collectively resist deformation when the interface is under the influence of the vacuum force, the plurality of particles are readily movable with respect to each other within the interface when at atmospheric or positive pressure.

6. The medical device of claim 5, wherein the plurality of particles are each formed with a uniform geometry.

7. The medical device of claim 5, wherein the plurality of particles are each irregularly shaped.

8. The medical device of claim 5, wherein the plurality of particles are formed with one or more shapes selected from a brick, a cube, a sphere, an ovoid, a pyramid, a cone, a step, or a cylinder.

9. The medical device of claim 1, wherein remaining portions of the catheter not including the expandable portion are configured to remain at a nominal outer diameter when the first and second layers within the expandable portion are radially expanded to a radially expanded configuration.

10. The medical device of claim 1, further comprising a stress relief feature disposed upon the catheter wall at an end of the expandable portion.

11. The medical device of claim 1, wherein the second lumen establishes fluid communication with the interface around an entire circumference of the distal end portion.

12. The medical device of claim 1, wherein the retention member is a compressible foam disposed within the interface between the first and second layers within the distal end portion, wherein in use when the vacuum force is applied a size of the compressible foam decreases and a rigidity of the compressible foam increases under the influence of the vacuum force applied to the interface from the second lumen, and the compressible foam is biased to expand and decrease rigidity when at or above atmospheric pressure.

13. The medical device of claim 1, further comprising an expandable balloon that is selectively positioned within the first lumen in registry with the distal end portion, wherein expansion of the balloon is configured to urge a corresponding radial expansion of the distal end portion.

14. The medical device of claim 13, wherein the retention member is configured to remain in the dense configuration when the balloon is deflated.

15. The medical device of claim 13, wherein the balloon further comprises a second portion that extends through the first lumen of the catheter, and wherein the balloon and the second portion can be slidably removed from the first lumen when the balloon is deflated.

16. The medical device of claim 13, wherein a second balloon is selectively positioned within the first lumen with a space between the second balloon and the expandable balloon.

17. The medical device of claim 16, wherein the expandable balloon and the second balloon are each configured to be selectively inflated and deflated from a same fluid source.

18. The medical device of claim 1, wherein the distal end portion of the catheter is expandable to increase a diameter of the distal end portion from a nominal diameter with application of a radial force upon the inner surface of the first layer, and wherein the distal end portion of the catheter is biased to return toward the nominal diameter when the radial force is removed and when the retention member is in the less dense configuration.

* * * * *